United States Patent [19]

Schock et al.

[11] Patent Number: 5,254,097
[45] Date of Patent: Oct. 19, 1993

[54] COMBINED PERCUTANEOUS CARDIOPULMONARY BYPASS (PBY) AND INTRA-AORTIC BALLOON (IAB) ACCESS CANNULA

[75] Inventors: Robert B. Schock; John J. Lucas, both of Sparta; William C. Corrigan, Jr., Randolph; Manuel L. Capinpin, Bayonne, all of N.J.

[73] Assignee: Datascope Investment Corp., Montvale, N.J.

[21] Appl. No.: 817,399

[22] Filed: Jan. 6, 1992

[51] Int. Cl.$^5$ .............................................. A61M 5/178
[52] U.S. Cl. .................... 604/167; 604/256; 604/284
[58] Field of Search ............. 604/284, 83, 86, 247, 604/256, 167, 169

[56] References Cited

U.S. PATENT DOCUMENTS

| | | | |
|---|---|---|---|
| 4,000,739 | 1/1977 | Stevens | 128/214.4 |
| 4,121,585 | 10/1978 | Becker, Jr. | 604/86 |
| 4,122,858 | 10/1978 | Schiff | 128/348 |
| 4,197,848 | 4/1980 | Garrett | 604/83 X |
| 4,261,339 | 4/1981 | Hanson et al. | 128/1 D |
| 4,287,892 | 9/1981 | Schiff | 128/349 B |
| 4,327,709 | 5/1982 | Hanson et al. | 128/1 D |
| 4,596,557 | 6/1986 | Pexa | 604/284 |
| 4,804,365 | 2/1989 | Litzie et al. | 604/4 |
| 5,098,385 | 3/1992 | Walsh | 604/256 X |

OTHER PUBLICATIONS

Bavaria, Effect of Circulatory Assist Devices on Stunned Myocardium, Ann. Thorac. Sug., 49:123-128 (1990).
Phillips, Percutaneous Cardiopulmonary Bypass and Innovations in Clinical Counterpulsation, Critical Care Clinics, vol. 2, No. 2 (Apr. 1986).
Check-Flo ® II Introducer Sets, Copyright Cook, Inc., 1989.
Cordis Sheath Introducers, Cordis Corporation, Dec. 1988.

*Primary Examiner*—John D. Yasko
*Attorney, Agent, or Firm*—Fitzpatrick, Cella, Harper & Scinto

[57] ABSTRACT

A cannula for performing two or more medical procedures either individually, seriatim or simultaneously, for example, combined percutaneous PBY and IAB procedures, which cannula includes a body having a common leg and two or more access port legs (e.g. a Y-shaped body), one access port for performing one procedure, a second access port for performing a second procedure, and hemostasis structure. A smooth continuous blood flow path is formed by a common lumen of a common leg of the cannula body and a primary lumen formed in a primary access port leg of the cannula body. The secondary access port legs are provided with secondary lumens that communicate with the common lumen.

53 Claims, 3 Drawing Sheets

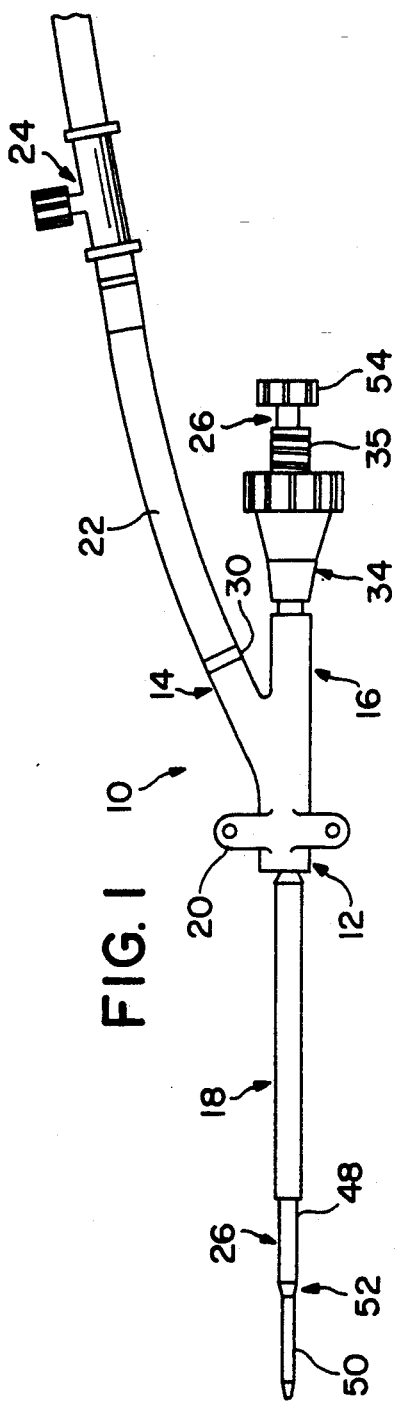
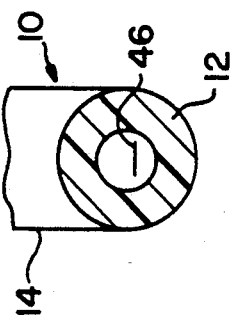
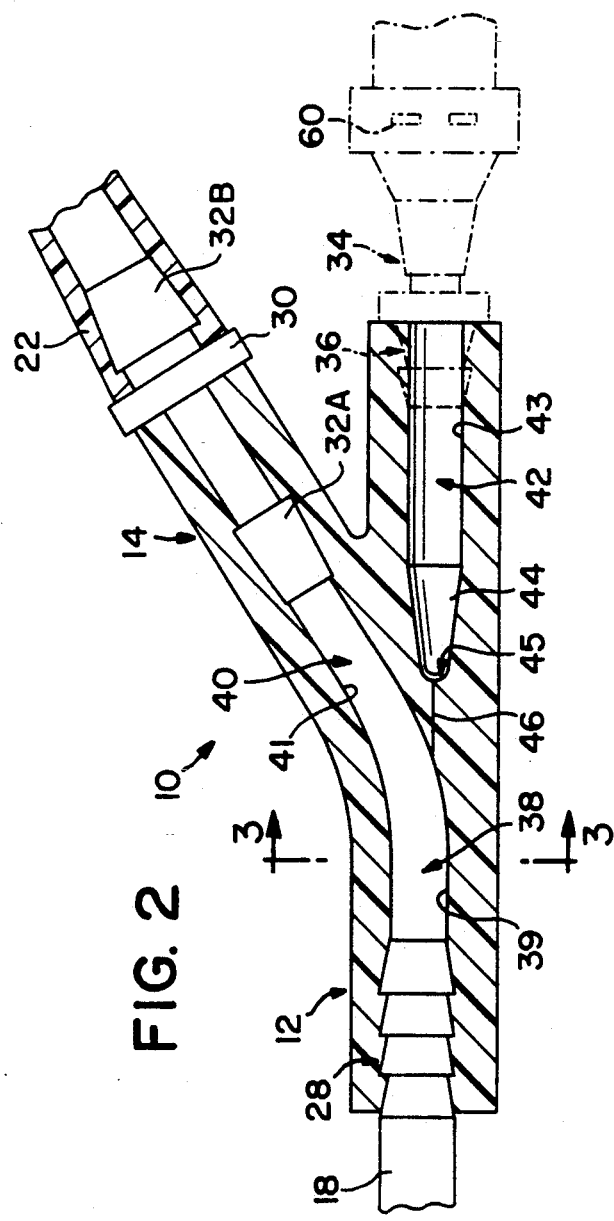

COMBINED PERCUTANEOUS CARDIOPULMONARY BYPASS (PBY) AND INTRA-AORTIC BALLOON (IAB) ACCESS CANNULA

BACKGROUND OF THE INVENTION

1. Field of the Invention

The present invention relates generally to a medical device and the procedures for employing that device. More particularly, it relates to a cannula with multiple access ports for performing multiple simultaneous medical procedures. The present invention has particular utility in a combined procedure involving percutaneous cardiopulmonary bypass (PBY) augmented by intra-aortic balloon (IAB) counterpulsation. Of course, the cannula of the present invention may be used with equal advantage in many other procedures and combined procedures.

2. Description of the Prior Art

Percutaneous cardiopulmonary bypass (PBY) cannulae and procedures are known. For example, U.S. Pat. No. 4,804,365 (Litzie, et al.) relates to vascular cannulae for transfemoral cardiopulmonary bypass. When performing PBY, deoxygenated blood is removed through a first cannula inserted in a femoral vein of one of the patient's legs. The deoxygenated blood is fed to an external oxygenator and pump system, and then pumped back into the patient through a second cannula inserted in a femoral artery of one of the patient's legs. A number of practitioners and researchers in the field believe that one of the drawbacks of PBY is its tendency to increase back pressure in the aorta, thereby increasing the load on the heart muscle during systole.

Counterpulsation, also known as intra-aortic balloon pumping (IABP), using intra-aortic balloon (IAB) catheters is well known. For example, U.S. Pat. No. 4,261,339 (Hanson, et al.) describes an IAB catheter designed for counterpulsation therapy. Datascope Corp., the assignee of this Hanson et al. patent as well as of the present invention, markets several IAB catheters.

For percutaneous intra-aortic balloon counterpulsation, an IAB normally is inserted into the body through a femoral artery in the groin area of the patient. The IAB then is pushed up through the arterial tree until the balloon is located in the descending thoracic aorta. Inflation and deflation of the balloon causes a pumping action that supplements the natural pumping of the heart. Inflation of the balloon forces blood out of the aorta to other parts of the body. Deflation of the balloon creates a slightly lowered pressure in the aorta, which reduces the back-pressure against which the heart must work during the next pumping cycle.

Recently, research has suggested that counterpulsation, when employed concurrently with cardiopulmonary bypass may counteract, at least in part, the increased aortic pressure produced by PBY. (See, e.g., Bavaria, J.E., et al., "Effect of Circulatory Assist Devices on Stunned Myocardium," *Annals of Thoracic Surgery* 1990, 49:123-8; and Phillips, S.J., "Percutaneous Cardiopulmonary Bypass and Innovations in Clinical Counterpulsations," *Critical Care Clinics*, Vol. 2, No. 2, April 1986.)

Heretofore, PBY and IAB, if done by means of percutaneous insertions, have each required a separate puncture in the femoral artery. Such percutaneous puncture wound insertion sites are preferably located in the groin area of the patient's thigh where the femoral artery is closest to the surface of the skin and most easily accessible. However, access to the femoral artery in this area is limited and gaining access through two separate puncture wounds can be difficult. Two puncture wounds present other problems as well, including increased trauma, increased risk of infection and bleeding. Thus, it would be advantageous to be able to perform PBY and IABP simultaneously through a single percutaneous puncture wound.

It also is frequently the case that the physician is unable to determine in advance whether both procedures will be necessary or whether one or the other will suffice. It would, therefore, be advantageous for the physician to be able, for example, to initiate PBY and decide later whether to insert an IAB. A multi-port cannula according to the present invention provides that flexibility.

Y-shaped cannulae and cannula adapters for providing multiple access ports through a single insertion site are known. U.S. Pat. No. 4,287,892 (Schiff) describes such a device designed specifically for use with intra-aortic balloon (IAB) catheters. However, the device described in the Schiff patent is made solely for surgical procedure, not for percutaneous insertion. In addition, the cannula described in the Schiff patent must have an IAB catheter resident therein at all times.

In order to give the physician the flexibility of being able to decide, after insertion of the cannula, whether to use only one of the access ports or more than one, means must be provided to prevent bleeding through those access ports not in use. This can be accomplished by incorporating one or more hemostasis valves in the cannula structure.

Of course, it is known to use a hemostasis valve integral with an introducer sheath. Known hemostatic valves generally include passive self-closing valves, "open hole" valves and "active" valves.

A passive self-closing valve generally is a one-way valve designed to seal about a catheter or other intra-aortic device inserted therethrough, and to close upon itself when there is no device inserted therethrough. An example of a passive self-closing valve is a duck-bill valve. Such valves have particular utility in applications that require passive sealing of passages having a fluid pressure differential across the valve. However, a duck-bill valve generally permits insertion only from one direction, i.e., from the low pressure side. Also, the sizing of the duck-bill opening generally provides effective sealing for devices falling within a limited size range. If it is necessary to insert different devices having widely varying sizes, for example, a guide wire followed by an IAB catheter, the duck-bill valve may not be ideally suited for the task.

An open-hole valve is a two-way valve. Examples include O-ring inserts and perforated diaphragms. Such valves, however, generally provide effective sealing only when the insertion device is resident therein. Therefore, an obturator cap, heparin drip, heparin lock, or similar device is needed to prevent leaks when no catheter or other device is inserted therethrough.

An active valve may be a one-way or two-way valve that is opened or closed by manipulating the valve or one or more of its components. An example is a Touhy Borst valve. Such valves have particular utility where a user needs to provide a seal under changing conditions.

It is also known to use an introducer cannula having a hemostatic valve and a port arranged for introducing fluids to the cannula or blood vessel. For example, U.S. Pat. No. 4,000,739 (Stevens) describes a hemostasis cannula comprising a body having a passage therethrough adapted to receive a catheter and a pair of juxtaposed gaskets mounted in the passage. The first gasket forms a seal around a catheter enclosed within the cannula; the second gasket is compressed against the first to seal the passage when the catheter is removed. The cannula also features a flexible entrance tube and a port for flushing the cannula chamber (e.g., a heparin drip), or for introducing fluids into a patient's blood vessel (e.g., anesthetic or intravenous feeding solution).

SUMMARY OF THE INVENTION

In order to overcome the above discussed drawbacks of prior devices the present invention provides a percutaneously insertable cannula having multiple access ports, the insertion of which cannula requires only a single vessel puncture.

The cannula of the present invention permits the physician to employ only one therapeutic procedure or several simultaneously. For example, the physician may use PBY alone or IABP alone or use the two procedures seriatim or simultaneously.

Another advantage of the present invention is that it permits the physician to decide, after one of the procedures, e.g. PBY, has been initiated whether to employ the other procedure. For example, the physician need not make this decision prior to gaining access to an artery, when the need for the second, third, fourth, etc., procedure may not be readily determinable.

The instant invention further provides a device and procedure whereby one or more of several therapies can be initiated and terminated as time and the dictates of the case require.

Another feature of the instant invention is that it permits initiation and termination of the several procedures with a minimal loss of blood and air entrainment.

The present invention and these and many other attendant features and advantages thereof will be readily and more completely appreciated with reference to the following detailed description of several embodiments taken together with the accompanying drawings.

BRIEF DESCRIPTION OF THE DRAWINGS

FIG. 1 is a plan view of a combined percutaneous cardiopulmonary bypass (PBY) and intra-aortic balloon (IAB) access cannula of the present invention with a sheath extension and a dilator resident therein.

FIG. 2 is an enlarged longitudinal cross-sectional view of the Y-shaped cannula body of FIG. 1.

FIG. 3 is a cross-sectional view of the cannula body depicted in FIG. 2, taken along line 3—3.

DETAILED DESCRIPTION OF THE PREFERRED EMBODIMENTS

Figure 4:
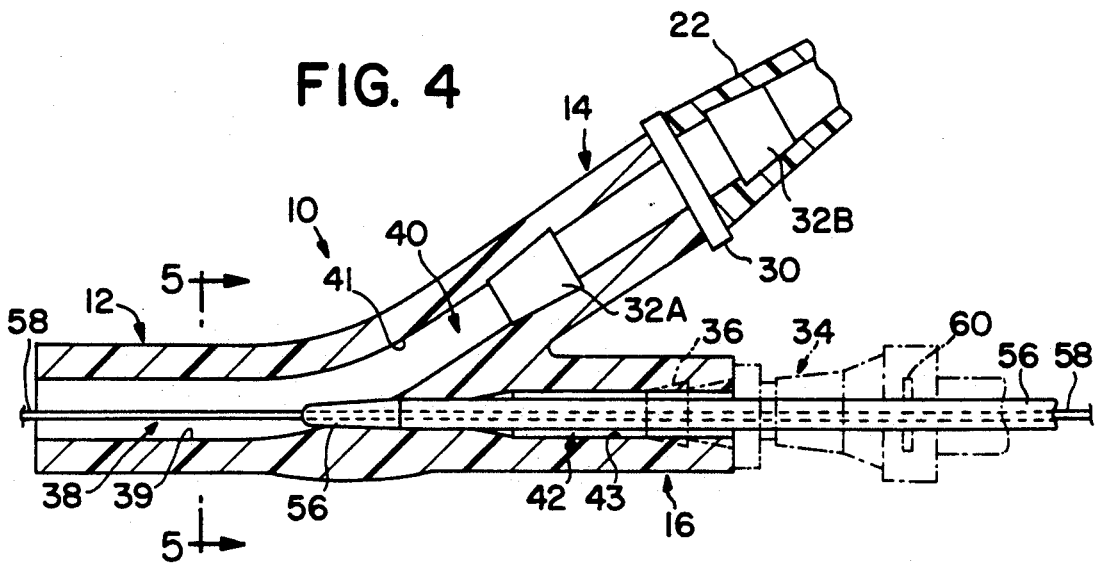
FIG. 4 is an enlarged longitudinal cross-sectional view of the Y-shaped cannula body of FIG. 1 with a secondary device in the process of being inserted over a guide wire through the access port and hemostatic valve of the cannula.

Referring now to the drawings, wherein like reference numerals identify like or corresponding parts throughout, FIGS. 1 to 6 illustrate one embodiment of a cannula according to the present invention designed to permit two procedures, for example PBY and IABP, to be employed simultaneously without the need for multiple puncture wounds. More particularly, as shown in FIGS. 1 to 6, the cannula includes a Y-shaped cannula body 10 having a common leg 12, a primary access port leg 14 arranged in fluid communication with common leg 12, and a second access port leg 16 arranged substantially co-axial with common leg 12.

Figure 6:
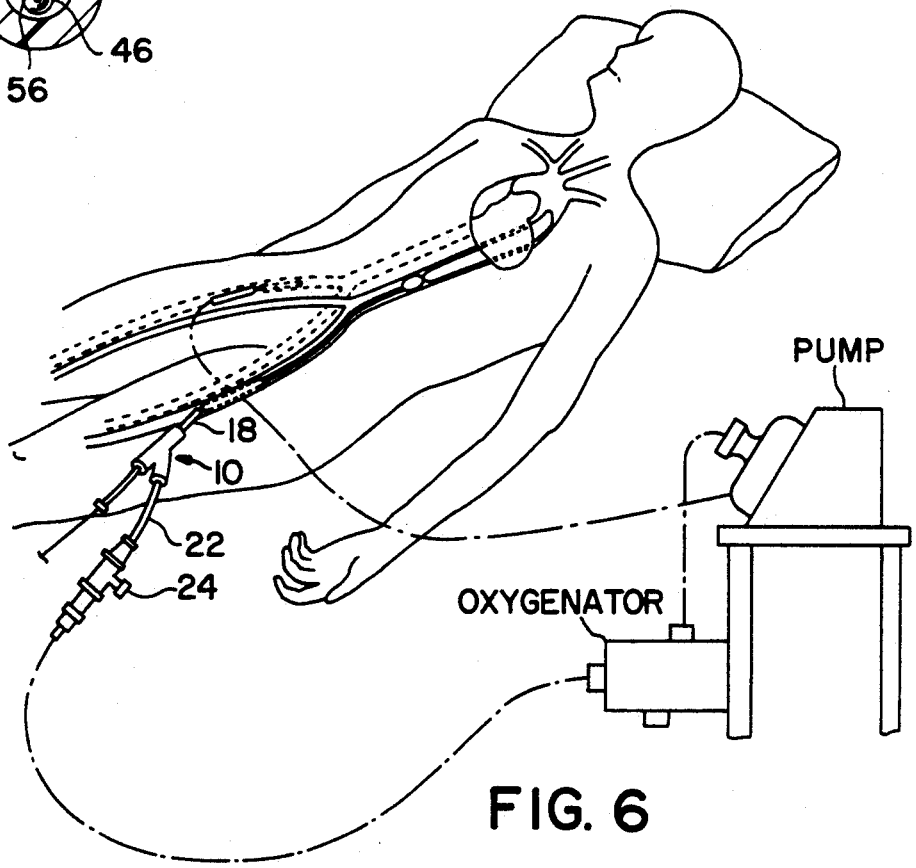
FIG. 6 is a diagrammatic sketch of a cannula of the present invention arranged for a combined percutaneous cardiopulmonary bypass and intra-aortic balloon counterpulsation procedure.

Referring particularly to FIG. 1, common leg 12 is provided with sheath extension 18, which is an extended intravascular cannula arranged for percutaneous insertion into the lumen of a patient's femoral artery (see, FIG. 6). Sheath extension 18 may be composed of any biologically compatible material that is suitable for percutaneous insertion, but is preferably a polyurethane tube. Common leg 12 also may be provided with a bracket 20 for securing the cannula to the patient's body.

Leg 14 serves as a first access port, for example, for reintroduction of oxygenated blood during PBY, and can be provided with or connected to an arterial return tube 22. A vented fitting 24 also may be provided. The arterial return tube 22 and vented fitting 24 may be attached to an external oxygenator and pump system for an extracorporeal cardiopulmonary bypass procedure (see, FIG. 6).

Leg 16 serves as a second access port for optional insertion of a secondary device, such as an IAB catheter. Also, as shown in FIG. 1, the second access port may provide a path for insertion of a dilator 26, to facilitate percutaneous insertion of sheath extension 18 into the patient's femoral artery (see discussion below of insertion procedure).

Referring now to FIGS. 1 and 2, in one embodiment the Y-shaped cannula body 10 is a one-piece flexible body composed of a biologically compatible material (e.g. a USP Class IV material). In this embodiment the Y-shaped cannula body 10 is most advantageously made of a clear or translucent elastomeric material, such as silicone rubber. As will be readily apparent from the discussion below, this composition provides flexibility to facilitate safe and efficient blood flow and access for secondary devices.

Initially, the clear or translucent material composition of the Y-shaped cannula body facilitates safe use by allowing visual monitoring of blood flow through the cannula. Thus, formation of any gas bubbles or blood clots may be detected during PBY procedure.

The elastomeric structure also facilitates safe and efficient sealing of various connectors to the Y-shaped body 10. For example, in the embodiment of FIGS. 1 to 6, sheath extension 18 is provided at one end with a radial barbed fitting 28. Radial barbed fitting 28 forms a secure seal between sheath extension 18 and common leg 12 of the Y-shaped cannula body 10. Likewise, tube connector 30 is provided at both ends with radial barbed fittings 32A, 32B, for forming a secure seal between the arterial return tube 22 and leg 14 of the Y- shaped body 10. Finally, threaded hub 34 is provided with radial barbed fitting 36 for forming a secure seal between threaded hub 34 and leg 16 of the Y-shaped body 10 (shown in phantom in FIG. 2).

Referring specifically to FIGS. 2 and 3, the Y-shaped cannula body 10 includes a continuous blood flow path (PBY access) and an integral self-sealing passive hemostatic valve for permitting introduction of a secondary device, e.g., an IAB catheter, without risking significant blood loss either before its introduction, during its introduction or while it is resident in the body. Common leg 12 includes a common lumen 38, circular in cross-section, and defined by a common lumen wall 39. Primary access port leg 14 includes a primary lumen 40, also circular in cross-section, and defined by a primary lumen wall 41. As can be seen, primary lumen 40 is in fluid communication with common lumen 38, and a smooth, continuous surface is provided at the transition from primary lumen 40 to common lumen 38.

The sizes and cross-sectional shapes of lumens 38 and 40 may vary, but generally are selected to provide an optimum blood flow range during both PBY procedure and optional combined PBY and IAB procedure. In one embodiment, common lumen 38 and primary lumen 40 each have an inner diameter of 0.22 inch. However, selection of the optimum sizes for any given application will be obvious to those skilled in the art of PBY cannulation.

Leg 16 serves as a second access port and includes a secondary lumen 42, circular in cross section, and defined by a secondary lumen wall 43. The secondary lumen 42 is provided at its distal end with a hemostatic valve disposed between secondary lumen 42 and common lumen 38. The hemostatic valve may be a single valve type or a combination of valve types selected according to the desired application. In the embodiment of FIGS. 1 to 6, the hemostatic valve includes a substantially conical portion 44, a semi-spherical portion 45 and a puncture or slit portion 46. Referring specifically to FIG. 2, the semi-spherical portion 45 terminates the distal end of conical portion 44, and has an arcuate perforation that is in registration with slit portion 46, which, in turn, extends through the common lumen wall 39 to the common lumen 38. Slit portion 46 lies in a plane substantially parallel to the axis of the common lumen 38, and at an angle to the axis of the primary lumen 40 of access port leg 14. Thus, it will be appreciated that this arrangement forms a combined open-hole valve and integral duck-bill valve between the secondary lumen 42 and the common lumen 38. As can best be seen in FIG. 4, even when the duck-bill valve is opened to permit passage therethrough of a catheter device, the valve does not occlude the blood path between primary access port leg 14 and common leg 12. Since slit portion 46 of the hemostatic valve is formed integral with common lumen wall 39, it will be appreciated that the hemostatic valve of the embodiment of FIGS. 1 to 6 does not interfere with the smooth flow of blood through the blood flow path formed by common lumen 38 and primary lumen 40. It also will be appreciated that, as shown in FIG. 2, this integral duck-bill arrangement is self-closing when no secondary device such as an IAB catheter is in use. The integral arrangement facilitates hemostatic sealing of the second access port because blood flow through the blood flow path maintains a pressure differential across the valve and tends to compress the flat sides of the slit portion 46 of the duck-bill valve. Finally, it will be appreciated that the perforated semi-spherical portion 45 acts as an open-hole valve to seal about any catheter or other intra-aortic device inserted therethrough.

The sizing of secondary lumen 42, conical portion 44, semi-spherical portion 45 and slit portion 46 is selected to provide optimum accessibility for secondary devices, such as IAB catheters, and to provide a substantially fluid-tight seal both with and without such devices resident therein. In one embodiment, secondary lumen 42 has a 0.190 inch inner diameter; conical portion 44 is approximately 0.300 inches in length and has a taper angle of approximately 30°; semi-spherical portion 45 has a 9 French inner diameter; and slit portion 46 is approximately 0.150 inch long, and 0.028 inch wide. However, selection of the optimal sizes of the several components will vary from case to case and application to application.

Figure 7:
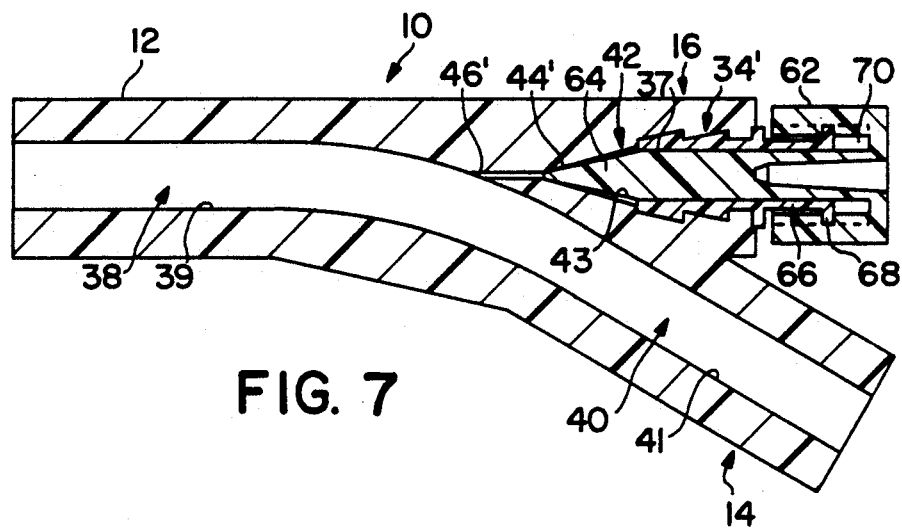
FIG. 7 is an alterative embodiment of the flexible Y-shaped cannula depicted in FIGS. 1 to 5, including an access port hub and access port cap/obturator assembly.

Referring now to FIG. 7, in an alternative embodiment the flexible Y-shaped cannula body 10 may comprise a hemostatic valve including a conical portion 44' and a slit portion 46' (i.e., no spherical portion). In this embodiment, for example, secondary lumen 42 has a 0.193 inch inner diameter; conical portion 44' has a 0.30 inch length with approximately a 30° angle taper; and slit portion 46' has a 0.150 inch length.

It will be appreciated that the present invention is a medical device and that use of the device is regulated by the FDA. The present invention is designed to be practiced by physicians trained and experienced in using percutaneous cannulation techniques (e.g., Seldinger technique).

In a preferred procedure, the patient is prepared using the customary preparations for percutaneous catheterization. Specifically, an angiographic needle (not shown) is percutaneously inserted into the femoral artery located in the patient's groin or upper thigh (see, FIG. 6). A safety guide wire is inserted through the angiographic needle into the artery, and the angiographic needle is removed, leaving the safety guide wire in place in the artery.

With dilator 26 resident in the cannula and extending beyond the end of sheath extension 18, the cannula is inserted into the artery by sliding it down over the guide wire. Referring again to FIG. 1, in one embodiment, dilator 26 is a one-piece flexible tube having a continuous lumen passing therethrough. Dilator 26 may be composed of any biocompatible material suitable for percutaneous medical procedures, but is most preferably made of a polyethylene. In the embodiment of FIG. 1, the lumen of dilator 26 has a constant 0.042 inch inner diameter for accepting a 0.030 to 0.038 inch diameter guide wire. As can be seen, the outer diameter of dilator 26 may be stepped to effect step-wise dilation of the artery upon insertion. In the embodiment of FIG. 1, dilator 26 includes a 13½ French main body 48 and a 1 to 2 inch distal end segment 50 ground to an 8 French outer diameter. Distal end segment 50 is most preferably about 2 inches in length to better facilitate tracking of the guide wire. An approximately ½ inch transition segment 52 also is provided between the main body 48 and distal end segment 50. Finally, dilator 26 also may have a screw cap 54, to cooperate with threads 35 of hub 34, to lock dilator 26 within the second access port of the cannula during insertion. During insertion, the arterial return tube to the first or primary access port preferably is clamped using, e.g., a hemostatic clamp such as a Roberts clamp (not shown).

As will be apparent to those skilled in the art, dilator 26 alternatively could be inserted through the first access port. This procedure may be preferred in applications where the hemostatic valve is sized for a small catheter or other intra-aortic device. Many valves provide a seal by stretching an elastomeric component about the inserted device and are limited in the amount they can be stretched before they retain a stretch "memory." Thus, insertion of dilator 26 during percutaneous insertion could cause a stretch memory that would prevent proper sealing of the valve over a later inserted intra-aortic device that has a smaller diameter or different configuration. Of course, where, as here, the hemostatic valve is self-closing, it is not necessary to clamp or otherwise obturate the second access port.

In applications where the hemostatic valve has retained a memory or otherwise is not self-closing, the secondary access port may be sealed by clamping or obturating during PBY procedure, or during percutaneous insertion using the first access port. For example, in the embodiment of FIG. 7, second access port leg 16 can be provided with a hub 34' configured for receiving an access port cap 62, which has attached to it an obturator 64. Specifically, access port hub 34' is provided with a lumen 37 therethrough, and a cylindrical fitting 66 for receiving obturator 64 of cap 62. Because hub 34' has a lumen, an IAB or other device can be inserted through it and, hence, it need not be removed. Fitting 66 includes a rim 68 which interlocks with access port cap 62 when the fitting is inserted in cylindrical recess 70. Thus, it will be appreciated that this geometry allows a practitioner to apply and remove access port cap 62.

As shown in FIG. 7, the distal portion of obturator 64 is conical in shape, and has a taper angle greater than the taper angle of conical portion 44'. When inserted in the hemostatic valve, obturator 64 substantially fills the conically shaped lumen of conical portion 44' and prevents leakage without producing a plunger effect that would push air or thrombus through the valve into the cannula blood flow path. It also prevents accumulation of blood in the hub lumen 34' that could thrombose over time.

One of the features of the present invention is that it permits the physician to (a) start PBY first and decide later whether to employ counterpulsation, (b) start counterpulsation first and later initiate PBY (c) initiate counterpulsation and PBY immediately following insertion of the cannula or (d) await further developments before initiating either procedure.

It is believed that in most instances the physician will elect to initiate PBY immediately and put off until a later time a decision on whether to begin counterpulsation. If counterpulsation is not to begin immediately, once sheath extension 18 is in the artery, dilator 26 normally would be unlocked from threaded hub 34, and the dilator 26 and safety guide wire would be withdrawn from the second access port. During initial insertion, access port leg 16 normally would be sealed off, e.g., with a stopcock or threaded cap (see above).

Once access to the artery has been obtained, any air in the arterial return tube 22 then normally would be vented using vented fitting 24, and the arterial return tube 22 would be attached to the extracorporeal oxygenator and pump using well known techniques (see FIG. 6). Finally, cannula body 10 would be secured to the patient's leg using bracket 20.

If, during PBY, it is decided that counterpulsation would be advantageous, PBY blood pumping normally would be momentarily interrupted and the IAB catheter would be inserted through secondary access port leg 16, common leg 12 and sheath extension 18. After the balloon portion of the IAB has exited sheath extension 18 PBY would be resumed.

If it has been decided that counterpulsation is to be initiated immediately, then normally only the dilator would be withdrawn, leaving the guide wire in place. The IAB then can be inserted over the guide wire. A guide wire 58 facilitating advancement of a secondary catheter device 56 is shown in FIG. 4. If counterpulsation is to proceed without simultaneous PBY, arterial return tube 22 to access port leg 14 normally will have to remain clamped or be maintained on heparin drip.

Figure 5:
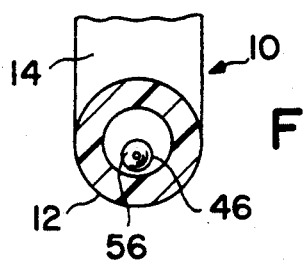
FIG. 5 is a cross-sectional view of the cannula body depicted in FIG. 4, taken along line 5—5.

Referring now to FIGS. 4 and 5, the Y-shaped cannula body 10 is shown having a secondary catheter device 56 inserted through the second access port leg 16 and the integral hemostatic valve. As shown in FIGS. 4 and 5, because the material from which the integral combined open-hole and duck-bill hemostatic valve is made is elastomeric, it forms a substantially fluid-tight seal about secondary catheter device 56. In addition, a secondary open hole valve can be provided in secondary lumen 42 or in threaded hub 34 to assure a fluid-tight seal when catheter 56 is resident therein. Such a secondary open hole valve might, for example, be in the form of perforated diaphragm 60 as depicted in FIG. 2. One or more annular seal rings (not shown) also could be used to act as an open hole valve.

It will be appreciated that there are a wide variety of catheter devices which could be inserted through access port leg 16. Some of those will have sufficient rigidity to allow the physician to push them through a duck-bill valve unassisted. However, others may have relatively fragile distal ends or otherwise may lack sufficient rigidity to be pushed unassisted through the integral hemostatic duck-bill valve. Therefore, an introducer having a continuous hollow passage therethrough may be inserted through access port leg 16 and the duck-bill valve, and the guide wire or catheter device 56 may be inserted through the lumen of the introducer. The introducer then may be withdrawn over the guide wire or catheter device, which remains resident therein.

From the above description, it will be appreciated that the embodiment of FIGS. 1 to 6 showing a combined PBY and IAB cannula according to the present invention provides multiple access ports for simultaneously pumping blood back into the femoral artery while counterpulsation is underway. It also provides an integral, self-closing, hemostatic valve which prevents blood loss or air entrainment when counterpulsation is not being employed and which prevents blood leakage around the catheter when an IAB is being inserted therethrough or is resident therein. Moreover, the single piece elastomeric construction of this arterial cannula resists crimping and buckling, minimizes the risk of bubble formation, blood clot formation and hemolysis.

Finally, it will be appreciated that this arterial cannula allows a clinician to perform, in any selected order or in combination, a percutaneous cardiopulmonary bypass procedure and a counter-pulsation procedure using a percutaneous intra-aortic balloon catheter.

Figure 8:
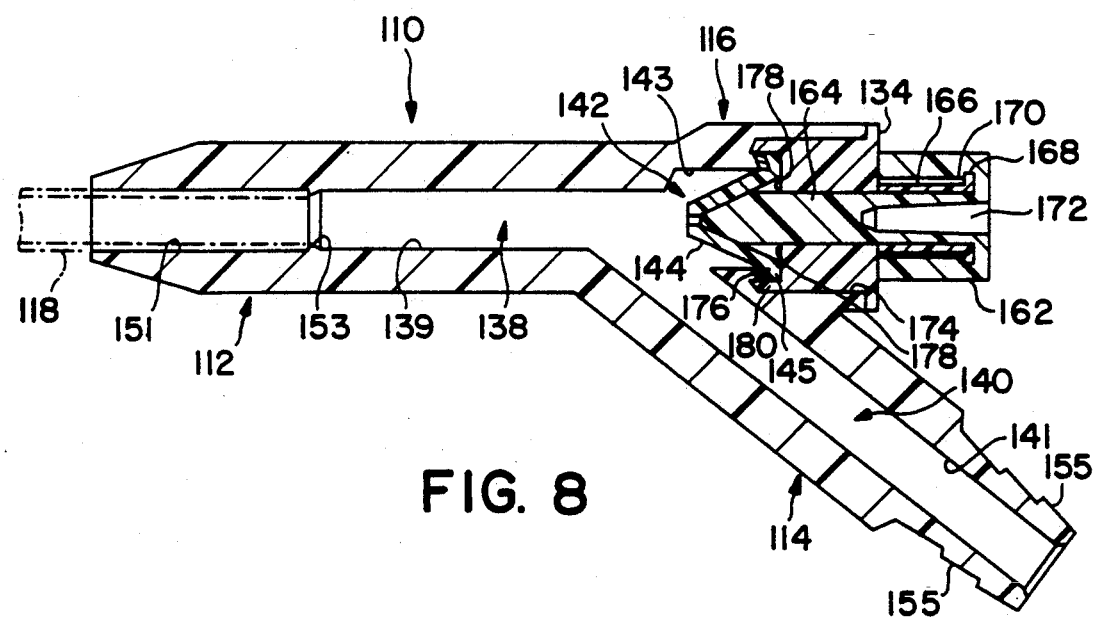
FIG. 8 is a longitudinal cross-sectional view of another embodiment of a cannula of the present invention having a rigid Y-shaped body.

In another embodiment of the present invention, also suitable for combined medical procedures such as combined PBY and IAB counterpulsation, the Y-shaped cannula body may be fabricated of a relatively rigid material. FIG. 8 illustrates an embodiment of a cannula according to the present invention having such a rigid Y-shaped body. As with the first embodiment, the embodiment of FIG. 8 is designed to permit two procedures, for example PBY and IABP, to be employed simultaneously without the need for multiple puncture wounds. More particularly, as shown in FIG. 8, the cannula includes a Y-shaped cannula body 110, having a common leg 112, a primary access port leg 114 arranged in fluid communication with common leg 112, and a second access port leg 116 arranged substantially co-axial with common leg 112.

In the present embodiment, Y-shaped cannula body 110 is a one piece rigid body composed of a biologically compatible material (e.g. a USP Class IV material). In this embodiment, Y-shaped cannula body 110 is believed to be most advantageously made of a lightweight, solid-plastic material, preferably rigid PVC, polycarbonate, or acrylic.

As those skilled in the art will readily appreciate, manufacture of molded rigid plastic or metal components can be automated and regulated to provide exact tolerances. Moreover, a rigid body can be adapted for a variety of applications by selecting from among various internal component parts having different characteristics, such as material composition, lumen size, valve type and valve opening size. Thus, an embodiment comprising a rigid Y-shaped body and selected internal components can provide closely controlled, tightly toleranced passages and efficient sealing about catheters and other devices inserted through such components.

Referring specifically to FIG. 8, rigid Y-shaped cannula body 110 includes a continuous blood flow path (normally this would be the PBY access) and a hemostatic valve for introduction of a secondary device, e.g., an IAB catheter, without risking significant blood loss or air entrainment. Common leg 112 includes a common lumen 138, circular in cross-section, and defined by a common lumen wall having two segments, proximal segment 139 and distal segment 151. Primary access port leg 114 includes a primary lumen 140, also circular in cross-section, and defined by a primary lumen wall 141. As shown therein, primary lumen 140 is in fluid communication with common lumen 138.

Common leg 112 also is adapted to receive a sheath extension 118 (shown in phantom in FIG. 8), e.g., an extended intravascular cannula arranged for percutaneous insertion into the lumen of a patient's femoral artery (see, discussion above). Specifically, proximal segment 139 has a diameter that is slightly smaller than that of distal segment 151, and a shoulder 153 is formed where the two meet. Shoulder 153 forms a seat for receiving sheath extension 118. Sheath extension 118 preferably should have an outer diameter such that a fluid tight friction fit exists between extension 118 and distal wall segment 151. As shown in FIG. 8, shoulder 153 may be angled to provide a substantially continuous transition of the blood flow path from common lumen wall 139 to the inner diameter of sheath extension 118. An annular recess (not shown) also could be provided adjacent to but just distal of shoulder 153, and an annular rib (not shown) could be formed at the proximal end of sheath extension 118 to snap into the recess.

Primary access port leg 114 is provided with exterior terminal barbs 155. Barbs 155 provide for a secure seal when a flexible elastic or plastic tubing, such as an arterial return tube is slid thereover (see discussion above).

As in the first embodiment, the sizes and cross-sectional shapes of lumens 138 and 140 may vary, but generally are selected to provide an optimum blood flow range during both PBY and combined PBY and IAB procedures. For example, common lumen 138 and primary lumen 140 each may have an inner diameter of approximately 0.20 inch. Of course, selection of the optimum sizes for any given application will be obvious to those skilled in the art.

Leg 116 serves as a second access port and includes a secondary lumen 142 defined by a secondary lumen wall 143. Secondary lumen 142 is provided at its distal end with a hemostatic valve disposed between secondary lumen 142 and common lumen 138.

The hemostatic valve may be a single valve type or a combination of valve types selected according to the desired application. In the embodiment of FIG. 8, a hemostatic valve assembly includes a perforated conical diaphragm 144, an access port hub 134 and an access port cap 162. In this embodiment, leg 116 is provided with a recess 174 for receiving conical diaphragm 144 and access port hub 134. Recess 174 includes a beveled annular ring 176 arranged concentric with secondary lumen 142. Conical diaphragm 144 is composed of an elastomeric material suitable for use in percutaneous procedures, preferably C-FLEX ™, and is provided with a beveled flange 145. Beveled flange 145 generally is selected to have a geometry complimentary to beveled annular ring 176, such that the two elements engage to form a fluid-tight seal.

Conical diaphragm 144 is supported in a fluid-tight seal relation with beveled annular ring 176 by access port hub 134. Specifically, access port hub 134 is provided with a circular recess 178, defined by annular seal ring 180, for receiving and engaging beveled flange 145 and beveled annular ring 176. It will be appreciated that compression of beveled flange 145 between beveled annular ring 176 and circular recess 178 also will cause beveled flange 145 to seat against annular seal ring 180 and, thus, to form a fluid-tight seal therewith.

Access port hub 134 may be composed of any biocompatible material suitable for use in percutaneous medical procedures, but is preferably composed of a rigid plastic material, most preferably ABS plastic. Those skilled in the art will appreciate that access port hub 134 may be secured within recess 174 of leg 116 by any conventional means, e.g., mating threads, friction fit, etc.

The size and shape of secondary lumen 142 is selected to accommodate conical diaphragm 144 when it is stretched to pass and seal about a secondary device inserted therethrough. For example, the diameter of secondary lumen 142 may be selected larger than the diameter of common lumen 138 by an amount equal to the thickness of conical diaphragm 144. Thus, it will be appreciated that, even when the conical diaphragm valve is opened to permit passage therethrough of a catheter device, the valve does not occlude the blood path between primary access port leg 114 and common leg 112.

Access port hub 134 also is provided with a cylindrical fitting 166 for receiving obturator 164 of access port cap 162. Cylindrical fitting 166 includes a rim 168 which interlocks cylindrical fitting 166 and access port cap 162 when inserted in cylindrical recess 170. Access port cap 162 also has a generally conical shaped recess 172, concentric with cylindrical recess 170. As in the first embodiment, this geometry allows a practitioner to apply and remove access port cap 162 by manual manipulation.

In a configuration similar to the above described obturator embodiment, the distal portion of obturator 164 is conical in shape, and has a taper angle greater than the taper angle of conical portion 144. When inserted in the hemostatic valve, obturator 164 substantially fills the conically shaped lumen of diaphragm 144 and prevents leakage without producing a plunger effect that would push air or thrombus through the valve into the cannula blood flow path. It also prevents accumulation of blood in the lumen of access port hub 134 that could thrombose over time.

Numerous other embodiments and modification will be apparent to those skilled in the art and all such obvious variants are intended to be covered by this patent. For example, the hemostatic valve may comprise one or more passive self-closing valves, open-hole valves, active valves (e.g., a Touhy Borst valve), or combinations thereof. Selection of a specific valve or combination of valves in accordance with a desired flexible or rigid Y-shaped cannula body application will be obvious to those skilled in the art. Also, the Y-shaped cannula body could comprise a rigid molded shell (e.g., plastic or metal) having internal components composed of biocompatible materials (e.g., USP Class IV plastic, rubber or elastomeric materials). These components, e.g., lumen walls and valves, may be configured and fixed by known methods, including, inter alia, fiction fitting, bonding, threading, interlocking, and combinations thereof.

In another aspect of the present invention, the cannula body could be configured to include three or more access ports, e.g., a combination of a primary access port and two or more secondary access ports, a combination of a secondary access port and two or more primary access ports, or a combination of two or more first access ports and two or more secondary access ports.

In other aspects of the present invention, the cannula may be used for combined percutaneous venous or surgical procedures. For example, during open-heart surgery it may be desirable to access the interior of the heart, coronary arteries or veins, or other arteries or veins for various medical procedures. A cannula of the present invention could be inserted through a puncture hole in an exposed heart chamber, artery or vein and, in a procedure similar to the percutaneous procedures described above, various catheters could be fed through the cannula and directed to the appropriate site for performing a combined medical procedure, e.g., coronary retroperfusion and bypass. Accordingly, the term percutaneous, as used herein, may include insertion of the cannula through a puncture in an artery or vein exposed during surgery. Other combined surgical or venous applications will be readily apparent to those skilled in the art.

It will be understood that the above description is illustrative only. It is not intended to limit the scope of the present invention. The following claims define the scope of protection and are to be interpreted in sufficient breadth as to cover and encompass all variants, modifications and alternatives which would reasonably occur to those of ordinary skill in the art.

What is claimed is:

1. A cannula adapted for percutaneous insertion into the body of a patient and comprising percutaneous insertion means and a cannula body, said cannula body comprising
   a common leg having a distal end, a proximal end and a common lumen therethrough defined by a common lumen wall, said common lumen being in fluid communication with said percutaneous insertion means,
   a primary access port leg having a primary lumen defined by a primary lumen wall, said primary lumen being in fluid communication with said common lumen and forming a continuous blood flow path therewith,
   a secondary access port leg having a secondary lumen defined by a secondary lumen wall, and
   hemostasis means for providing access for percutaneous insertion of a catheter through said secondary lumen and said blood flow path, and for preventing a blood flow from said blood flow path through said secondary lumen.

2. The cannula recited in claim 1, wherein said cannula body is formed of a flexible material.

3. The cannula recited in claim 1, wherein said cannula body is formed of a single-piece of elastomeric material.

4. The cannula recited in claim 1, wherein said hemostasis means comprises a hemostatic valve.

5. The cannula recited in claim 4, wherein said hemostatic valve comprises a passive self-closing valve.

6. The cannula recited in claim 4, wherein said hemostatic valve comprises a duck-bill valve.

7. The cannula recited in claim 4, wherein said hemostatic valve comprises an open-hole valve.

8. The cannula recited in claim 4, wherein said hemostatic valve comprises a perforated diaphragm valve.

9. The cannula recited in claim 4, wherein said hemostatic valve comprises an active valve.

10. The cannula recited in claim 4, wherein said hemostatic valve comprises a Touhy Borst valve.

11. The cannula recited in claim 1, wherein said hemostasis means comprises an obturator cap.

12. The cannula recited in claim 4, wherein a portion of said hemostatic valve forms an integral part of said common lumen wall.

13. The cannula recited in claim 12, wherein said hemostatic valve lies in a plane substantially in line with the common lumen and forms an angle with an axis of the primary lumen.

14. The cannula recited in claim 4, wherein said hemostatic valve comprises a conical portion, a semi-spherical portion and a slit portion, wherein a proximal end of the conical portion is in fluid communication with said secondary lumen, wherein said semi-spherical portion terminates a distal end of the conical portion, wherein said semi-spherical portion has an arcuate perforation therein, and wherein the slit portion is formed integral with the common lumen wall and is in registration with said arcuate perforation.

15. The cannula recited in claim 14, wherein the slit portion lies in a plane substantially parallel to the axis of the common lumen and forms an angle with an axis of the primary lumen.

16. The cannula recited in claim 1, wherein said percutaneous insertion means further comprises a sheath extension disposed at a distal end of said common leg.

17. The cannula recited in claim 1, wherein said percutaneous insertion means comprises a sheath extension in fluid communication with the common lumen, for percutaneous intravascular insertion.

18. The cannula recited in claim 4, wherein said secondary access port leg is substantially coaxial with said common leg.

19. The cannula recited in claim 18, wherein said secondary lumen has a distal end and a proximal end, and wherein said hemostatic valve is disposed at the distal end of said secondary lumen.

20. The cannula recited in claim 4, wherein said primary access port leg is substantially coaxial with said common leg.

21. The cannula recited in claim 20, wherein said secondary lumen has a distal end and a proximal end, and wherein said hemostatic valve is disposed at the distal end of said secondary lumen.

22. The cannula recited in claim 1, wherein said secondary lumen has a distal end and a proximal end, and wherein said hemostatic valve is disposed at the distal end of said secondary lumen.

23. The cannula recited in claim 1, wherein blood can enter said cannula, flow through said blood path from said primary lumen to said common lumen and out of said cannula when said catheter device is resident in said secondary lumen and in said common lumen.

24. The cannula recited in claim 23, wherein said secondary lumen has a distal end and a proximal end, and wherein said hemostatic valve is disposed at the distal end of said secondary lumen.

25. The cannula recited in claim 1, wherein said primary and secondary access port legs are disposed at a proximal end of said common leg.

26. The cannula recited in claim 4, wherein said hemostatic valve is disposed adjacent a proximal end of said common leg.

27. The cannula recited in claim 4, wherein said hemostatic valve is disposed between said secondary lumen and said common lumen.

28. The cannula recited in claim 4, wherein said hemostatic valve is disposed between said secondary lumen and said primary lumen.

29. The cannula recited in claim 1, wherein said cannula body is formed of a rigid material.

30. The cannula recited in claim 1, wherein said cannula body comprises a rigid body shell and internal components forming said common lumen wall, primary lumen wall, secondary lumen wall, and hemostasis means.

31. The cannula recited in claim 1, wherein said cannula body comprises a rigid body forming said common lumen wall, said primary lumen wall and said secondary lumen wall.

32. The cannula recited in claim 1, wherein said hemostasis means comprises a hemostatic valve selected from the group consisting of a passive self-closing valve, a duck-bill valve, an open-hole valve, a perforated diaphragm valve, an active valve, and a Touhy Borst valve.

33. The cannula recited in claim 2, wherein said hemostasis means comprises a hemostatic valve selected from the group consisting of a passive self-closing valve, a duck-bill valve, an open-hole valve, a perforated diaphragm valve, an active valve, and a Touhy Borst valve.

34. The cannula recited in claim 29, wherein said hemostasis means comprises a hemostatic valve selected from the group consisting of a passive self-closing valve, a duck-bill valve, an open-hole valve, a perforated diaphragm valve, an active valve, and a Touhy Borst valve.

35. The cannula recited in claim 30, wherein said hemostasis means comprises a hemostatic valve selected from the group consisting of a passive self-closing valve, a duck-bill valve, an open-hole valve, a perforated diaphragm valve, an active valve, and a Touhy Borst valve.

36. The cannula recited in claim 31, wherein said hemostasis means comprises a hemostatic valve selected from the group consisting of a passive self-closing valve, a duck-bill valve, an open-hole valve, a perforated diaphragm valve, an active valve, and a Touhy Borst valve.

37. The cannula recited in claim 29, wherein said hemostasis means comprises an obturator cap.

38. The cannula recited in claim 30, wherein said hemostasis means comprises an obturator cap.

39. The cannula recited in claim 31, wherein said hemostasis means comprises an obturator cap.

40. The cannula recited in claim 1, wherein said hemostasis means comprises at least two components selected from the group comprised of an obturator cap, a passive valve and an active valve.

41. The cannula recited in claim 1, wherein said hemostasis means comprises at least two components selected from the group comprised of an obturator cap, a duck-bill valve, an open-hole valve, and a perforated diaphragm valve.

42. A cannula adapted to permit passage therethrough of a catheter for percutaneous insertion in the body of a patient, and comprising a cannula body including
   a common leg having a common lumen defined by a common lumen wall, said common lumen being in fluid communication with percutaneous insertion means,
   at least one primary access port leg, each such primary access port leg having a primary lumen therein defined by a primary lumen wall, each said primary lumen being in fluid communication with the common lumen and forming a continuous blood flow path therewith,
   at least one secondary access port leg, each such secondary access port leg having a secondary lumen therein defined by a secondary lumen wall, and
   at least one hemostatic valve arranged to provide access for percutaneous insertion of a catheter through said at least one secondary lumen and said blood flow path, and to prevent a blood flow from said blood flow path through said at least one secondary lumen.

43. A cannula adapted for percutaneous insertion into the body of a patient comprising percutaneous insertion means and a cannula body, said cannula comprising
   a common leg having a distal end, a proximal end, and a common lumen therethrough defined by a common lumen wall,
   a first access port leg having a first lumen defined by a first lumen wall,
   first hemostasis means for preventing blood from exiting through said first access port leg when said leg is not in use,
   a second access port leg having a second lumen defined by a second lumen wall, and
   second hemostasis means for preventing blood from exiting through said second leg when said leg is not in use, wherein access to said common lumen can be gained through each of said first and second legs.

44. The cannula recited in claim 43, further comprising a third access leg.

45. The cannula recited in claim 44, further comprising hemostasis means for preventing blood from exiting through said third leg when said leg is not in use, and wherein access to said common lumen can be gained through said third leg.

46. The cannula recited in claim 44, further comprising a fourth access leg.

47. The cannula recited in claim 46, further comprising hemostasis means for preventing blood from exiting through said fourth leg when said leg is not in use, and wherein access to said common lumen can be gained through said fourth leg.

48. The cannula recited in claim 44, wherein each of said hemostasis means comprises a hemostasis valve.

49. The cannula recited in claim 45, wherein each of said hemostasis means comprises a hemostasis valve.

50. The cannula recited in claim 47, wherein each of said hemostasis means comprises a hemostasis valve.

51. The cannula recited in claim 48, wherein each said hemostasis valve is selected from the group consisting of a passive self-closing valve, a duck-bill valve, an open-hole valve, a perforated diaphragm valve, an active valve, and a Touhy Borst valve.

52. The cannula recited in claim 49, wherein each said hemostasis valve is selected from the group consisting of a passive self-closing valve, a duck-bill valve, an open-hole valve, a perforated diaphragm valve, an active valve, and a Touhy Borst valve.

53. The cannula recited in claim 50, wherein each said hemostasis valve is selected from the group consisting of a passive self-closing valve, a duck-bill valve, an open-hole valve, a perforated diaphragm valve, an active valve, and a Touhy Borst valve.

* * * * *

UNITED STATES PATENT AND TRADEMARK OFFICE
CERTIFICATE OF CORRECTION

PATENT NO. : 5,254,097

DATED : October 19, 1993

INVENTOR(S) : ROBERT B. SCHOCK, ET AL.

It is certified that error appears in the above-identified patent and that said Letters Patent is hereby corrected as shown below:

COLUMN 3

Line 65, "alterative" should read --alternative--.

COLUMN 6

Line 54, "step-wise" should read --stepwise--.

COLUMN 7

Line 47, "PBY (c)" should read --PBY, (c)--.

COLUMN 8

Line 63, "counter-pulsation" should read --counterpulsation--.

COLUMN 9

Line 55, "fluid tight" should read --fluid-tight--.

COLUMN 10

Line 26, "C-FLEX$_{TM}$," should read --C-FLEX$^{TM}$,--.
Line 28, "complimentary" should read --complementary--.

COLUMN 11

Line 14, "modification" should read --modifications--.

UNITED STATES PATENT AND TRADEMARK OFFICE
CERTIFICATE OF CORRECTION

PATENT NO. : 5,254,097
DATED : October 19, 1993
INVENTOR(S) : ROBERT B. SCHOCK, ET AL.

It is certified that error appears in the above-identified patent and that said Letters Patent is hereby corrected as shown below:

COLUMN 12

Line 23, "single-piece" should read --single piece--.

COLUMN 15

Line 19, "claim 44," should read --claim 43,--.

Signed and Sealed this

Third Day of May, 1994

Attest:

BRUCE LEHMAN

Attesting Officer     Commissioner of Patents and Trademarks